(12) United States Patent
Simmons et al.

(10) Patent No.: US 8,241,638 B2
(45) Date of Patent: *Aug. 14, 2012

(54) INDUCTION OF AN IMMUNE RESPONSE AGAINST DENGUE VIRUS USING THE PRIME-BOOST APPROACH

(75) Inventors: Monika Simmons, Germantown, MD (US); Kevin R. Porter, Boyds, MD (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 1320 days.

This patent is subject to a terminal disclaimer.

(21) Appl. No.: 11/982,488

(22) Filed: Nov. 2, 2007

(65) Prior Publication Data

US 2012/0135035 A1 May 31, 2012

Related U.S. Application Data

(60) Provisional application No. 60/860,233, filed on Nov. 9, 2006.

(51) Int. Cl.
*A61K 39/12* (2006.01)
(52) U.S. Cl. .................................................. 424/218.1
(58) Field of Classification Search ........................ None
See application file for complete search history.

(56) References Cited

U.S. PATENT DOCUMENTS

2004/0131594 A1 * 7/2004 McMichael et al. ......... 424/93.2

FOREIGN PATENT DOCUMENTS

WO    WO 03/097846    * 11/2003

OTHER PUBLICATIONS

Raviprakash et al (Virology 290:74-82, 2001).*
Lan Chen, Dan Ewing, Hemavathy Subramanian, Karla Block, Jonathan Rayner, Kimberly D. Alterson, Martha Sedegah, Curtis Hayes, Kevin Porter and Kanakatte Raviprakash. A Heterologous DNA Prime-Venezuelan Equine Encephalitis Virus Replicon Particle Boost Dengue Vaccine Regimen Affords Complete Protection from Virus Challenge in Cynomolgus Macaques Journal of Virology, Nov. 2007. vol. 81:11634-11639.
Putnak R, Barvir D, Burrous J, Dubois D, Dandrea V, Hoke C, Sadoff J, Eckels K, 1996. Development of a purified, inactivated dengue 2 virus vaccine prototype in Vero cells: immunogenicity and protection in mice and rhesus macaques. J Inf Dis 174:1176-1184.
Sun W, Edelman R, Kanesa-Thasan N, Eckels K, Putnak R, King A, Houng H, Tang D, Scherer J, Hoke C, Innis B, 2003. Vaccination of human volunteers with monovalent and tetravalent live-attenuated dengue vaccine candidates. Am.J. Trop. Med. Hyg. 69(6):24-31.

* cited by examiner

*Primary Examiner* — Mary E Mosher
(74) *Attorney, Agent, or Firm* — Joseph K. Hemby; Albert M. Churilla; Ning Yang

(57) ABSTRACT

The invention relates to methods for the induction of an immune response to dengue virus. The method of inducing an immune response against dengue virus comprises administration of a non-replicating immunogen followed by a boost with a tetravalent live attenuated viral vaccine. Another aspect of the inventive subject matter is a method of inducing an immune response against dengue virus using a heterologous prime-boost regimen with the priming immunogen comprising a DNA expression system, an adenovirus expression vector or a Venezuelan equine encephalitis virus replicon system and the boosting immunogen comprising the same without the DNA expression system. Each expression system contains DNA sequences encoding dengue viral proteins.

4 Claims, 2 Drawing Sheets

INDUCTION OF AN IMMUNE RESPONSE AGAINST DENGUE VIRUS USING THE PRIME-BOOST APPROACH

This application claims the benefit of provisional application 60/860,233, filed Nov. 9, 2006.

BACKGROUND OF INVENTION

1. Field of Invention

The inventive subject matter relates to a method of inducing an immune response against dengue virus using a prime-boost vaccination methodology.

2. Background

Dengue virus, the causative agent of dengue fever (DF) and dengue hemorrhagic fever (DHF), is a virus of the genus Flavivirus, a single-stranded enveloped RNA virus with positive polarity. Its RNA encodes approximately 3,400 amino acids. The virus exists as four antigenically-distinguishable serotypes.

Dengue fever is the most common human arbovirus infection worldwide and a serious public health concern accounting for estimates of 100 million infections annually (WHO 1986; Monath and Heinz 1996; Thomas, et al 2003). DF and DHF are found in most tropical areas including Africa, Asia, the Pacific, Australia, and the Americas.

Although the virus is capable of growing in a variety of species of mosquitoes, including Aedes albopictus, Aedes polynesiensis and Aedes scutellaris, Aedes aegypti is the most efficient mosquito vector because of its domestic habitat (Gubler 1988). Four antigenically distinct serotypes of dengue virus have been identified with all causing human diseases (Gubler, et al 1979; Henchal and Putnak 1990). Each of the four serotypes, although distinct, is similar enough to the others to elicit only partial cross-protection following infection (WHO 1986). Following infection, viremia is typically detected early at the onset of symptoms (Halstead 1997). Although many dengue infections are mild, some infections result in DHF and dengue shock syndrome (DSS), which are potentially fatal. This usually occurs in a small number of people during a second infection caused by a dengue virus that is different from the virus causing the first infection (Halstead 1997).

Dengue virus infection occurs following the bite of dengue virus-infected Aedes mosquitoes, which were previously infected by feeding on infected humans. Symptoms of dengue infection include high fever, severe headache, retro-orbital pain, development of a rash, nausea, joint and muscle pain, and usually start within five to six days following the bite of an infected mosquito. Symptoms of DHF also include marked sub-dermal bleeding, causing a purplish bruise, as well as bleeding from the nose, gums, and gastrointestinal (GI) tract. The fatality rate associated with DHF is at 6 to 30% with most deaths occurring in infants. The management of DHF is symptomatic and supportive, and is aimed at replacement of fluid loss (Nimmannitya 1996).

It is not possible to make an accurate diagnosis of mild or classic DF based on clinical features alone since many symptoms of DF resemble those of other diseases, such as chikungunya infection (Nimmannitya 1996), measles, influenza, and rickettsial infections. Differential diagnosis must include malaria and other viral, bacterial, and rickettsial diseases. Diagnostic methods for infection are typically based on detection of virus, viral antigens, genomic sequences, and detection of dengue-specific antibodies (Shu and Huang 2004). DHF can, in some cases, be more accurately diagnosed based on clinical signs and symptoms, including high continuous fever for 2 to 7 days, hepatomegaly, hemoconcentration, shock and thromocytopenia.

Most infections result in DF, which is self-limiting. However, DHF and DSS are life-threatening. Although vaccines against other flaviviruses, such as yellow fever and Japanese encephalitis, have been licensed, there are currently no efficacious vaccines to protect against DF, DHF or DSS.

Two dengue tetravalent live-attenuated vaccine (TLAV) candidates currently exist. However, both of these vaccines may be either reactogenic or poorly immunogenic in some recipients. Promising alternatives include chimeric viruses (e.g., Yellow fever/Dengue), recombinant proteins, inactivated viruses and nucleic acid (DNA) vaccines. The DNA vaccines may be particularly useful at eliciting a cell-mediated as well as a humoral immune response.

Experimental evidence suggests that, in non-human primates, dengue DNA vaccines, given alone, require several booster administrations and long intervals between the administrations in order to induce protective immunity. Other non-replicating vaccines such as the purified inactivated vaccines can often induce high titers of neutralizing antibody but these vaccines may be poor inducers of long-term immunological memory. Therefore, a safe, efficacious immunization method and composition is needed for the more timely induction of long-lasting immunity to dengue virus infection.

BRIEF SUMMARY OF INVENTION

The invention relates to methods of inducing an immune response against dengue virus. The inventive subject matter is a method for the induction of immune response against dengue virus with reduced reactogencity by priming the subject with a non-replicating immunogen and boosting with a tetravalent live attenuated viral vaccine. Examples of non-replicating immunogens include tetravalent DNA vaccines containing DNA sequences encoding dengue virus proteins or tetravalent purified inactivated dengue virus protein vaccines.

Further aspects of the invention include methods of inducing an immune response to dengue virus via heterologous prime-boost vaccination regimens. The priming and boosting compositions contain different expression systems encoding and expressing dengue viral proteins. The expressions systems include adenoviral expression vectors, DNA expression vectors, and Venezuelan equine encephalitis virus replicon expression systems.

DESCRIPTION OF PREFERRED EMBODIMENTS

Prime-Boost Method Using DNA/TPIV/TLAV

Figure 1:
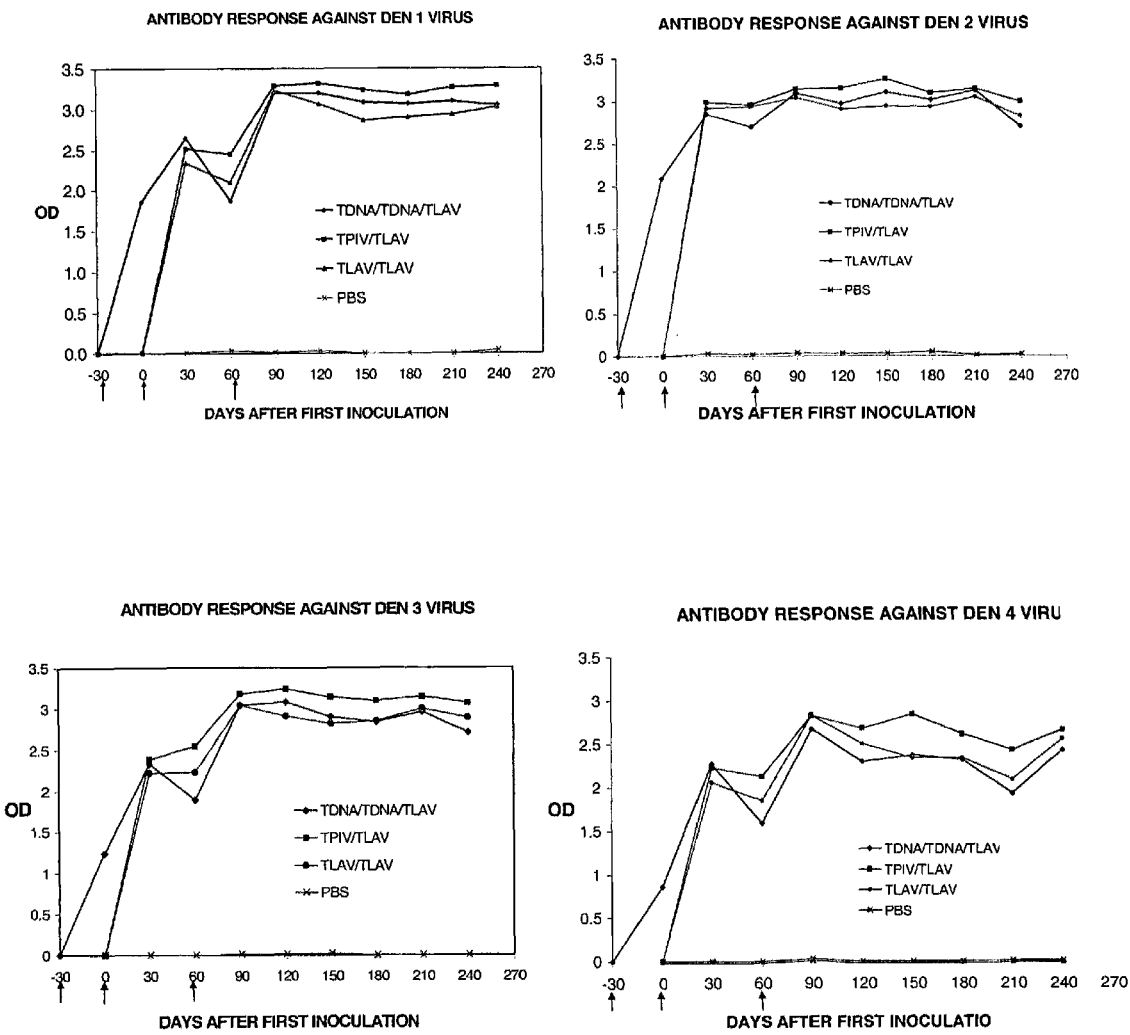
FIG. 1. Graphs illustrating serum immunoglobulin (IgG) antibody responses of non-human primates immunized with a tetravalent dengue DNA vaccine (TDNA), a tetravalent dengue purified inactivated vaccine (TPIV), followed by a tetravalent dengue live attenuated vaccine (TLAV). Samples were tested by ELISA at a 1:100 dilution.

A need exists for the induction of a long-lasting, efficacious immune response to dengue virus infection. To fulfill this critical need, the contemplated invention comprises immunizing methods that use dengue virus DNA or inactivated dengue virus proteins as a priming immunogen with live attenuated dengue virus as a boosting immunogen in a prime-boost immunization scheme (See Example 1 and 2). The resultant immune response has greater efficacy and safety.

Live attenuated viruses (LAV) often exhibit significantly elevated immune responses over other immune compositions, but also frequently exhibit detrimental reactogenicity. In order to improve the immunogenicity of anti-dengue vaccines, while reducing potential reactivity, an aspect of the current invention contemplates a method for the induction of immunity to dengue virus comprising administering a tetravalent DNA vaccine (TDNA) or a tetravalent purified inactivated vaccine (TPIV) as a priming immunogen followed by a boost with a tetravalent live attenuated viruse (TLAV). The inventive rationale is that priming with non-replicating vaccines, such as DNA or protein, will generate an immune response that will reduce reactogenicity and improve immunogenicity of the TLAV (See Example 1).

Heterologous Prime-Boost Method Using VEE Replicon/DNA Expression Vector/Adenovirus Expression Vector The invention also contemplates the use of a Venezuelan equine encephalitis virus (VEE) replicon or adenovirus vector to express dengue virus proteins as either a prime or a boost, which is described in detail in Example 3. In the contemplated inventive immunization methods, either adenovirus expression vectors, DNA expression vector or VEE replicon, with each containing dengue virus DNA sequences comprise the prime immunization. Subsequent to the prime immunization, a heterologous boost is administered either as an adenovirus expression vector or VEE replicon, with each containing sequences coding for dengue virus proteins (See table 2).

EXAMPLES

Example 1

Composition and Method of Inducing Anti-Dengue Response Using TDNA/TPIV/TLAV

Groups of rhesus macaques (N=4) were primed with either two (2) doses of TDNA, one dose of TPIV, or one dose of TLAV, followed by boosting with TLAV. The dengue TLAV was made by serial passage of four wild-type monovalent virus isolates in primary dog kidney (PDK) cells. The passaged viruses were tested in rhesus monkeys where they induced significantly lower levels of viremia compared with unpassaged wild-type parent viruses. They were then propagated in fetal rhesus lung (FRhL) cells and combined to make the TLAV formulation. The inventive formulation contemplates that any combination of dengue virus strains and proteins can be utilized. A preferred embodiment, illustrated in this example, consists of DEN 1 PDK 27, DEN 2 PDK 50, DEN 3 PDK 20 and DEN 4 PDK 6.

The TDNA can consist of DNA sequences or constructs encoding any dengue protein. A preferred embodiment, is illustrated in this example, consists of the pre-membrane (prM) and envelope (E) genes of DEN 1 West Pac, DEN 2 wild-type/Phil+lysosome associated membrane protein (LAMP) domain, DEN 3 wild-type/Phil, and DEN 4 wild-type/Phil. The DEN 2 construct has a replacement of the C-terminal transmembrane and cytoplasmic domains of E with LAMP.

Similarly, TPIV can be a combination of one or more purified inactivated dengue virus proteins. As an illustration, in a preferred embodiment, the TPIV consists of the core protein (C), pre-membrane (prM), envelope (E) and nonstructural protein 1 (NS1) of DEN 1 (West Pac), DEN 2 (S16803), DEN 3 (CH53489) and DEN 4 (TVP-360). The viruses were grown in Vero cells, purified, inactivated with formalin and adsorbed onto 0.1% aluminum hydroxide.

Figure 2:
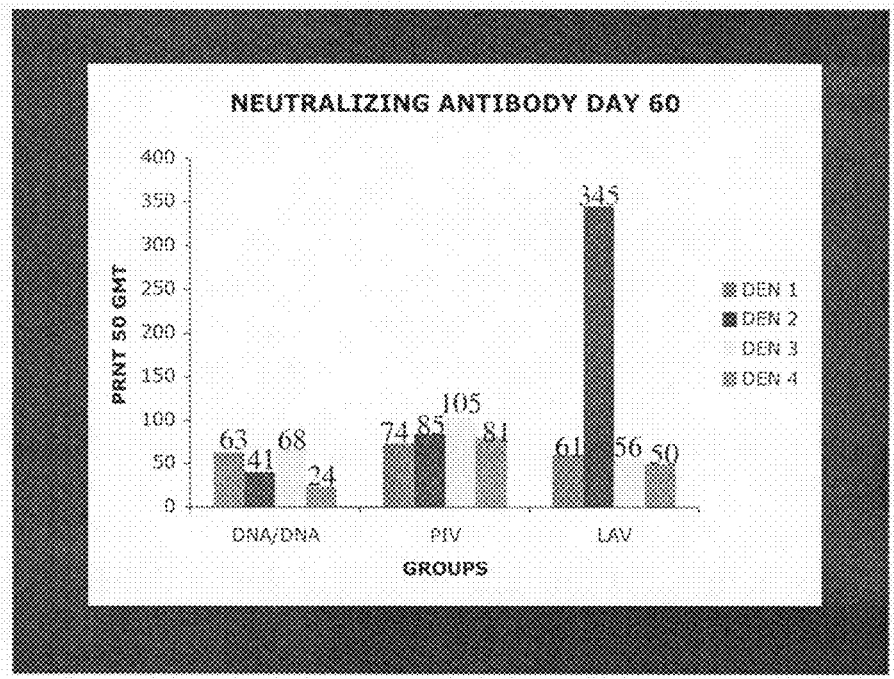
FIG. 2. Bar graphs illustrating neutralizing antibody on day 60 following immunization of monkeys with a tetravalent dengue DNA vaccine (TDNA), a tetravalent dengue purified inactivated vaccine (TPIV), and a tetravalent dengue live attenuated vaccine (TLAV).

Referring to FIG. 1, antibody responses measured by ELISA demonstrated tetravalent immune responses and high titers of dengue-specific IgG in all groups, which were maintained until the day of challenge. Referring to FIG. 2, low-titered virus-neutralizing antibodies (Nab) were demonstrated against DEN-1, DEN-3 and DEN-4 after priming in all vaccine groups. Nab against DEN-2 were highest in animals that received the TLAV (GMT=1216) followed by groups that received TPIV (GMT=347) and TDNA (GMT=126). Nab titers peaked one month after the TLAV booster and then declined over time in all groups. The most persistent tetravalent Nab titers were observed with the TPIV/TLAV regimen.

Six months after the booster vaccination, all vaccinated animals and an unvaccinated control group were challenged with live, non-attenuated DEN-3 virus. As shown in Table 1, serum viremia was measured for 10 days after the live virus challenge to evaluate protection. Complete protection against viremia was observed in the TLAV/TLAV group and the TPIV/TLAV group. Three of four animals in TDNA/TDNA/TLAV group exhibited 1 to 3 days of viremia (mean=1.5 days) compared with unvaccinated controls, which had 4.75 mean days of viremia. Measurement of virus Nab titers 14 days after challenge showed a 2-5 fold and 2-10 fold increase in the TPIV/TLAV and TLAV/TLAV groups respectively, whereas the TDNA/TLAV regimen resulted in a 6-53 fold increase.

TABLE 1

Viremia After Challenge

| Group | Monkey | \multicolumn{10}{c}{Days of viremia} | Mean days of viremia (for grp) |
| --- | --- | --- | --- | --- | --- | --- | --- | --- | --- | --- | --- | --- |
|  |  | 1 | 2 | 3 | 4 | 5 | 6 | 7 | 8 | 9 | 10 |  |
| DNA/DNA/LAV | A71 | − | − | − | − | − | − | + | − | − | − |  |
|  | 856Z | − | − | − | − | − | − | − | − | − | − |  |
|  | 894Z | + | − | + | − | − | − | − | − | − | − |  |
|  | 922Z | − | − | − | − | + | + | + | − | − | − | 1.5 |
| PIV/LAV | 890Z | − | − | − | − | − | − | − | − | − | − |  |
|  | A63Z | − | − | − | − | − | − | − | − | − | − |  |
|  | 916Z | − | − | − | − | − | − | − | − | − | − |  |
|  | A96Z | − | − | − | − | − | − | − | − | − | − | 0.0 |

TABLE 1-continued

| Viremia After Challenge | | | | | | | | | | | | |
|---|---|---|---|---|---|---|---|---|---|---|---|---|
| | | Days of viremia | | | | | | | | | | Mean days of viremia |
| Group | Monkey | 1 | 2 | 3 | 4 | 5 | 6 | 7 | 8 | 9 | 10 | (for grp) |
| LAV/LAV | P146 | − | − | − | − | − | − | − | − | − | − | |
| | 860Z | − | − | − | − | − | − | − | − | − | − | |
| | 3158 | − | − | − | − | − | − | − | − | − | − | |
| | 928Z | − | − | − | − | − | − | − | − | − | − | |
| | | | | | | | | | | | | 0.0 |
| SAL/SAL | 914Z | + | + | + | + | + | + | − | − | − | − | |
| | B85 | − | + | − | − | − | − | + | − | + | + | |
| | 868Z | − | + | + | − | − | + | + | + | − | − | |
| | 898Z | − | + | + | + | + | − | − | − | − | − | |
| | | | | | | | | | | | | 4.75 |

The conclusion from these studies demonstrate that priming with TPIV resulted in increased vaccine immunogenicity and protective efficacy compared to priming with TDNA, and did not prevent effective boosting with TLAV.

Example 2

Prophetic Use of TDNA/TPIV/TLAV to Induce Human Immunity

An aspect of the current invention is a method of administering TDNA/TPIV followed by TLAV formulation to humans in order to induce an anti-dengue immune response. The TDNA, TPIV and TLAV can be composed from any dengue gene sequence or strain, as illustrated in Example 1.

Other methods of administration may be used. However, as an illustration of the contemplated inventive method, the following prophetic example is disclosed as a preferred embodiment. In the prophetic example, the TDNA is administered intramuscularly as a total of 5 mg (1.25 mg/serotype) using the needle-free Biojector. The TDNA is given as two doses, one month apart. The TPIV is given as only one dose of 4 ug (1 ug/serotype) intramuscularly, using a needle and syringe. The TLAV is given as 5 logs/serotype subcutaneously using a needle and syringe.

Example 3

Prophetic Examples of Prime/Boost Immunization Using VEE Replicon, Adenovirus Expression System, or DNA Expression System Compositions The contemplated immunization method comprises a number of potential prime/boost compositions using VEE replicon, adenovirus expression system or a DNA expression system, each system containing dengue gene sequences. Preferred compositions and combinations of prime-boost are illustrated in Table 2.

TABLE 2

| Combinations of prime-boost Compositions | |
|---|---|
| Prime | Boost |
| DNA expression system | Adenovirus expression vector |
| VEE replicon system | Adenovirus expression vector |
| DNA expression system | VEE Replicon system |
| Adenovirus expression vector | VEE replicon system |

For example, the adenovirus expression vector, listed in Table 2 can be any adenoviral expression vector. The contemplated adenoviral expression vector has the E1 and E4 genes removed, which are replaced with the pre-membrane (prM) and envelope (E) genes from either DEN 1 and DEN 2 or DEN 3 and DEN 4. The contemplated adenoviral composition, therefore, is administered either as a single adenoviral vector expressing genes from only two dengue strains (i.e., DEN 1 and 2 or 3 and 4) or a mixture of 2 adenoviral vectors with one expressing DEN 1 and 2 and the other vector expressing DEN 3 and 4.

The DNA expression system is any suitable DNA expression system capable of in vivo expression. A preferred system is pVR1012 (see U.S. Pat. No. 6,455,509 to Kochel, et al). In this composition, a DNA sequence or construct encoding dengue membrane and envelope genes for either DEN 1, 2, 3 or 4 are inserted into the plasmid. The composition, therefore, is either a single plasmid containing genes to a single dengue strain or a mixture of 2 or more plasmids with each containing genes from different strains of dengue.

Similar to the DNA expression system, the Venezuelan equine encephalitis (VEE) replicon system (VRP) contains pre-membrane and envelop proteins from either of DEN 1, 2, 3 or 4. Like the DNA vaccine composition, the VRP composition is either a single VRP containing genes to a single dengue strain or a mixture of 2 or more VRP systems with each containing genes from different strains of dengue. The dengue prM and E genes are cloned into a plasmid vector containing the VEE genome, replacing the VEE capsid and glycoprotein genes. This recombinant plasmid contains all the sequences (except the VEE capsid and glycoprotein) for packaging the RNA into replicon particles. Two other plasmids, one each containing the VEE capsid and the glycoprotein genes provide the missing elements in trans, and form parts of the tripartite (three-plasmid) system. RNA is prepared from each of the three plasmids by in vitro transcription.

A mixture of all 3 RNAs is used to transfect BHK (baby hamster kidney) cells. The RNAs are translated into proteins in the transfected cells. The transfected BHK cells then produce VRPs into which the recombinant RNA containing dengue genes has been packaged. These VRPs are purified and used as a vaccine. The dengue-VRP vaccines can infect cells but can not propagate new progeny.

Example 4

Vaccination Using a DNA Expression System/VEE Replicon Prime/Boost Composition As an illustration, a candidate vaccine D1ME-VRP expressing dengue virus type 1 pre-membrane (prM) and envelope (E) proteins from a Venezuelan equine encephalitis virus (VEE) replicon system was constructed. Three vaccination regimens (DIME DNA vaccine, D1ME-VRP, and a heterologous prime-boost vaccine with DIME DNA as the prime immunogen and DD1ME-VRP as the boost immunogen) were compared for immunogenicity and protection against dengue-1 virus challenge in a non-human primate model.

Groups of 3 and 4 cynomolgus macaques were immunized with three doses of DIME DNA vaccine (DDD), three doses of D1ME-VRP (VVV) or with two doses of DNA priming vaccine and third booster dose of D1ME-VRP (DDV). A control group of animals was inoculated with PBS. Virus neutralizing antibody was measured by plaque reduction neutralization test (PRNT) and 50% neutralization titers (PRNT-50) were determined by probit analysis. T cell responses were measured by gamma-IFN ELISPOT. Measured 4 weeks after final immunization, the DDV group produced the highest virus neutralizing antibody titers (PRNT-50=2304) followed by VVV (PRNT-50=1405) and DDD (PRNT-50=1364) groups. However, moderate T cell responses were demonstrated only in DDD and DDV vaccinated animals.

Five months after the final dose, all animals were challenged with live dengue-1 virus and viremia was determined by infecting Vero cells with sera collected from daily bleeds. All three (3) control animals became viremic for 6-7 days (mean=6.3 days). All vaccination regimens showed significant protection from viremia. DDV immunized animals were completely protected from viremia (mean=0 days). DDD and VVV vaccinated animals had mean days of viremia of 0.66 and 0.75, respectfully. Thus, the antibody response and protection elicited from D1ME-VRP was comparable to those elicited from D1ME-DNA vaccine. However, the prime-boost approach resulted in higher antibody responses and complete protection.

References

1. Gubler, D. J., S. Nalim, R. Tan, H. Saipan, and J. Sulianti Saroso. 1979. Variation in susceptibility to oral infection with dengue viruses among geographic strains of *Aedes aegypti*. Am. J. Trop. Med. Hyg. 28:1045-1052.
2. Gubler, D. I. 1988. Dengue. In *The Arboviruses: Epidemiology and Ecology*. T. P. Monath (ed.), CRC Press (Boca Raton), p 223-260.
3. Halstead, S. B. 1997. Epidemiology of dengue and dengue hemorrhagic fever. In Dengue and Dengue Hemorrhagic Fever. D. J. Gubler and G. Kuno, editors. Cab International, London. 23-44.
4. Henchal, E. A. and J. R. Putnak. 1990. The dengue viruses. Clin. Microbiol. Rev. 3:376-396.
5. Monath, T. P., and F. X. Heinz. 1996. Flaviviruses. *In* Fields Virology. B. N. Fields, D. M. Knipe and P. M. Howley, (eds.) Lippincott-Raven, Philadelphia. 961-1034.
6. Nimmannitya, S. 1996. Dengue and dengue haemorrhagic fever. *In* Manson's Tropical Diseases. G. C. Cook (eds.) W.B. Saunders Company, Ltd (London). 721-729.
7. Shu, P. Y., and J. H. Huang. 2004. Current advances in dengue diagnosis. Clin. Diagn. Lab. Immunol., 11(4):642-650.
8. World Health Organization. *Dengue Hemorrhagic Fever: Diagnosis, Treatment and Control*. Geneva: WHO, 1986.

Having described the invention, one of skill in the art will appreciate in the appended claims that many modifications and variations of the present invention are possible in light of the above teachings. It is therefore, to be understood that, within the scope of the appended claims, the invention may be practiced otherwise than as specifically described.

What is claimed is:

1. A method of inducing immunity against dengue virus comprising administering a priming dengue virus immunogen comprising a tetravalent purified inactivated vaccine and a boosting dengue virus immunogen comprising a tetravalent live attenuated viral vaccine, wherein said live attenuated viral vaccine comprises a live attenuated dengue virus representing any strain of Dengue serotypes 1-4.

2. The method of claim 1, wherein said boosting immunogen is administered between two weeks and 2 months of said administration of said priming immunogen.

3. The method of claim 1, wherein the prime administration further comprising an adjuvant.

4. The method of claim 3, wherein said adjuvant is aluminum hydroxide.

* * * * *